United States Patent
Matsumoto

(10) Patent No.: US 9,606,135 B2
(45) Date of Patent: Mar. 28, 2017

(54) AUTOMATED BIOCHEMICAL ANALYZER AND REAGENT CONTAINER

(71) Applicant: Toshiba Medical Systems Corporation, Otawara-shi (JP)

(72) Inventor: Satoshi Matsumoto, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/826,568

(22) Filed: Aug. 14, 2015

(65) Prior Publication Data

US 2015/0355210 A1 Dec. 10, 2015

Related U.S. Application Data

(63) Continuation of application No. PCT/JP2014/051975, filed on Jan. 29, 2014.

(30) Foreign Application Priority Data

Feb. 15, 2013 (JP) .................................. 2013-027908
Jan. 29, 2014 (JP) .................................. 2014-013849

(51) Int. Cl.
  *G01N 35/02* (2006.01)
  *G01N 35/04* (2006.01)
  (Continued)

(52) U.S. Cl.
  CPC ............ *G01N 35/025* (2013.01); *B01L 3/527* (2013.01); *G01N 35/1002* (2013.01);
  (Continued)

(58) Field of Classification Search
  CPC ....... G01N 2035/0451; B01L 2200/028; B01L 3/527
  See application file for complete search history.

(56) References Cited

U.S. PATENT DOCUMENTS 5,651,941 A * 7/1997 Stark .................... B01L 9/06
                                               220/676
2001/0028863 A1 10/2001 Kitagawa
(Continued)

FOREIGN PATENT DOCUMENTS

JP    2002-48803 A    2/2002
JP    2005-164509 A   6/2005
(Continued)

OTHER PUBLICATIONS

Translation of JP 2010-139412 to Toshiba Corp., Reagent Container, Automatic Analysis System, and Reagent Management Method, published Jun. 24, 2010.*

(Continued)

*Primary Examiner* — P. Kathryn Wright
(74) *Attorney, Agent, or Firm* — Oblon, McClelland, Maier & Neustadt, L.L.P.

(57) ABSTRACT

An embodiment of an automated biochemical analyzer is configured to dispense a first reagent, a second reagent, and a sample into a reaction cell to measure a compound liquid thereof. The automated biochemical analyzer includes a first reagent container, a second reagent container, a reagent rack, and a driver. The first reagent container and the second reagent container each include a support and retain the first reagent and the second reagent, respectively. The supports are configured to be connectable to and disconnectable from each other. The reagent rack holds the first reagent container and the second reagent container and allows the first reagent container and the second reagent container to be disconnected for analysis. The driver moves the first reagent container and/or the second reagent container such that the supports are connected to each other upon extraction of the first reagent container and the second reagent container.

2 Claims, 7 Drawing Sheets

(51) Int. Cl.
  *G01N 35/10*    (2006.01)
  *B01L 3/00*     (2006.01)
  *G01N 35/00*    (2006.01)

(52) U.S. Cl.
  CPC .. *B01L 2200/028* (2013.01); *G01N 35/00732* (2013.01); *G01N 2035/0451* (2013.01); *G01N 2035/0455* (2013.01)

(56) References Cited

U.S. PATENT DOCUMENTS

| | | |
|---|---|---|
| 2005/0142040 A1 | 6/2005 | Hanawa et al. |
| 2011/0223682 A1 | 9/2011 | Wakamiya |

FOREIGN PATENT DOCUMENTS

| | | |
|---|---|---|
| JP | 2008-180639 A | 8/2008 |
| JP | 2010-139412 A | 6/2010 |
| JP | 2011-153990 A | 8/2011 |
| JP | 2011-191062 A | 9/2011 |

OTHER PUBLICATIONS

International Search Report issued Apr. 15, 2014 for PCT/JP2014/051975 filed on Jan. 29, 2014 in English Language.

\* cited by examiner

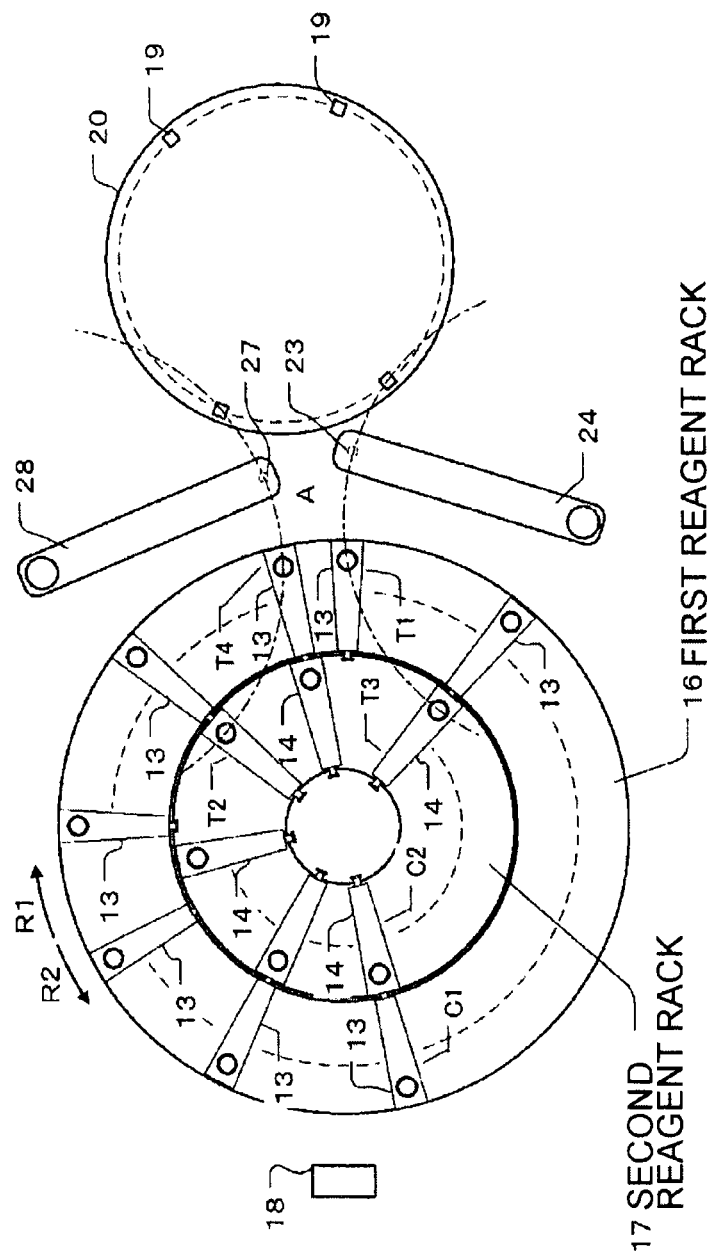

AUTOMATED BIOCHEMICAL ANALYZER AND REAGENT CONTAINER

CROSS-REFERENCE TO RELATED APPLICATION

This application is based upon and claims the benefit of priority from Japanese Patent Applications No. 2013-027908, filed Feb. 15, 2013 and No. 2014-013849, filed Jan. 29, 2014; the entire contents of which are incorporated herein by reference.

FIELD

Embodiments described herein relate generally to an automated biochemical analyzer and a reagent container.

BACKGROUND

An automated biochemical analyzer is used for the analysis of biochemical test assays, immune test assays, and the like. The automated biochemical analyzer optically measures a change in color tone and turbidity caused by the reaction of a stirrer of a sample taken from a subject and a reagent used for the analysis of a test assay. Based on this measurement, the automated biochemical analyzer generates analysis data that is represented by the concentration or density of a variety of test assay components in the sample, enzyme activity, and the like.

The automated biochemical analyzer analyzes a test assay selected according to the test after storing reagent containers in a reagent storage. The reagent containers include a container for retaining a first reagent of one-reagent system, a container for retaining a first reagent of two-reagent system, and a container for retaining a second reagent that is paired up with the first reagent. Then, the automated biochemical analyzer aspirates a sample from a sample container by a sample dispensing probe and dispenses it into a reaction cell, and aspirates the reagent from the reagent container by a reagent dispensing probe and dispenses it into the reaction cell. The automated biochemical analyzer measures the stirrer of the sample and the reagent dispensed into the reaction cell.

Generally, reagents of two-reagent system are used for most test assays. Some reagents of two-reagent system have to be used in a predetermined combination of a lot of the first reagent and a lot of the second reagent. Accordingly, if at least one of the first reagent and the second reagent is insufficient in the reagent containers stored in the reagent storage and there is a need to replace both the reagents, it is required to find and retrieve the two reagent containers from the reagent storage for the replacement. This is time consuming.

BRIEF DESCRIPTION OF THE DRAWINGS

FIG. 3 is a plan view of first and second reagent racks that hold first and second reagent containers in the embodiment.

DETAILED DESCRIPTION

Figure 1:
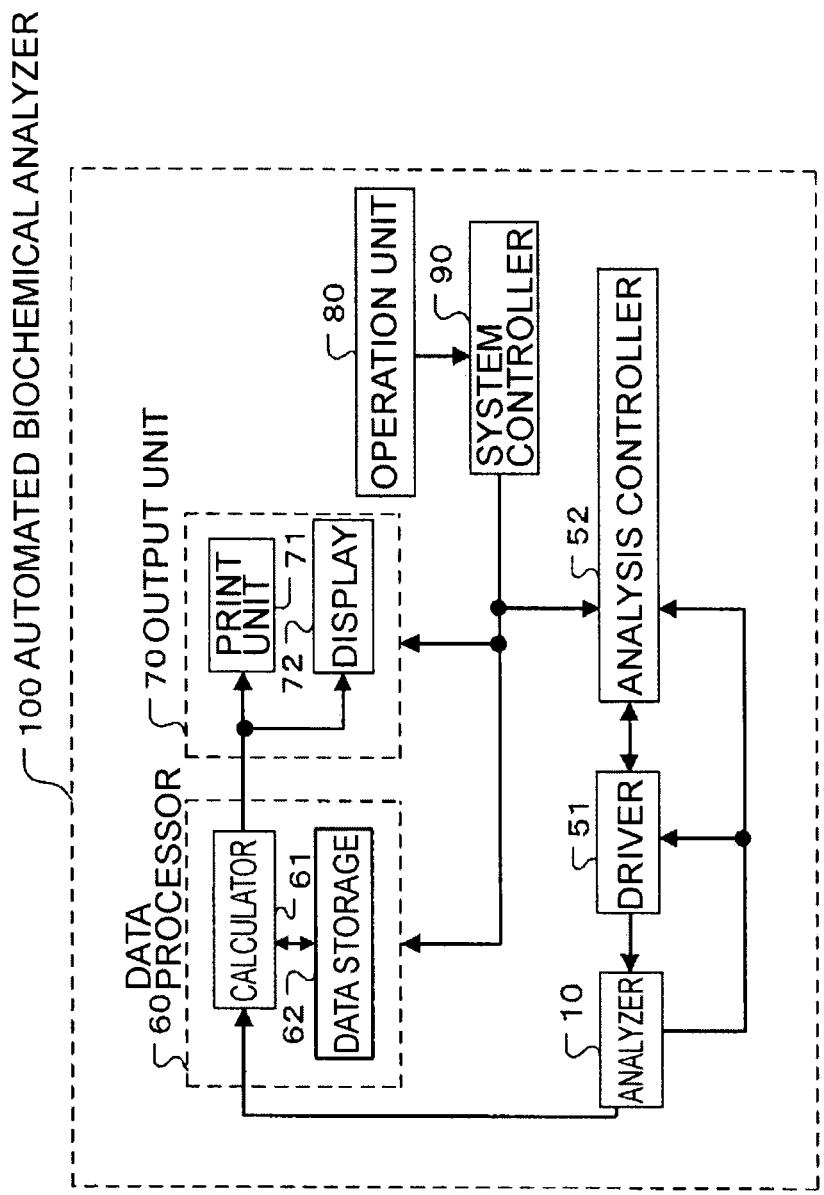
FIG. 1 is a block diagram of an automated biochemical analyzer according to an embodiment.

In general, according to one embodiment, an automated biochemical analyzer is configured to dispense a first reagent, a second reagent, and a sample into a reaction cell to measure a compound liquid of them. The automated biochemical analyzer includes a first reagent container, a second reagent container, a reagent rack, and a driver. The first reagent container and the second reagent container each include a support and retain the first reagent and the second reagent, respectively. The supports are configured to be connectable to and disconnectable from each other. The reagent rack holds the first reagent container and the second reagent container and allows the first reagent container and the second reagent container to be disconnected from each other for analysis. The driver moves the first reagent container and/or the second reagent container such that the supports are connected to each other upon extraction of the first reagent container and the second reagent container.

Referring now to the drawings, a description is given of an automated biochemical analyzer according to embodiments.

FIG. 1 is a block diagram illustrating a configuration of an automated biochemical analyzer according to an embodiment. An automated biochemical analyzer 100 includes an analyzer 10, a driver 51, and an analysis controller 52. The analyzer 10 measures a compound liquid of a standard sample or a test sample of each test assay and a reagent for the analysis of the test assay, and generates standard data or test data. The driver 51 drives each analysis unit involved in the measurement of the analyzer 10. The analysis controller 52 controls the driver 51.

The automated biochemical analyzer 100 further includes a data processor 60, an output unit 70, an operation unit 80, and a system controller 90. The data processor 60 generates calibration data and analysis data by processing the standard data and the test data generated by the analyzer 10. The output unit 70 outputs the calibration data and the analysis data generated by the data processor 60 by printing or displaying the data. The operation unit 80 is used to enter various command signals and the like. The system controller 90 collectively controls the analysis controller 52, the data processor 60, and the output unit 70.

Figure 2:
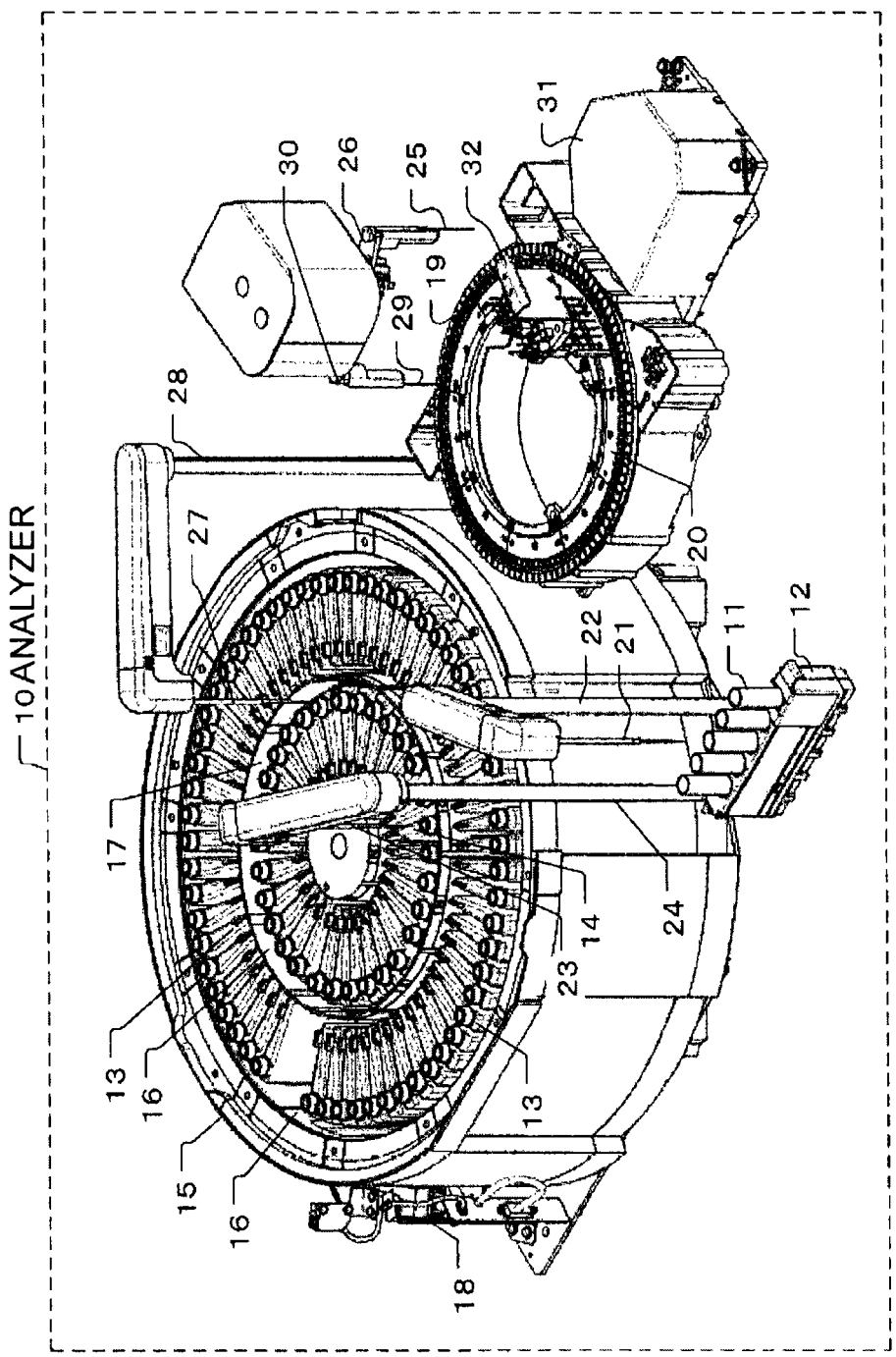
FIG. 2 is a perspective view of an analysis unit of the embodiment.

FIG. 2 is a perspective view illustrating the configuration of the analyzer 10. The analyzer 10 includes sample containers 11 to retain samples such as a standard sample and a test sample, and sample racks 12 for holding the sample containers 11. The analyzer 10 further includes first reagent containers 13, second reagent containers 14, a reagent storage 15, and a first reagent rack 16. Among reagents for the analysis of each test assay, for example, the first reagent containers 13 retain a first reagent of one-reagent system and two-reagent system. The second reagent containers 14 retain a second reagent that is paired up with the first reagent. The reagent storage 15 refrigerates the first reagent and the second reagent in the first reagent containers 13 and the second reagent containers 14. The first reagent rack 16 is located in the reagent storage 15 to hold the first reagent containers 13.

The analyzer 10 further includes a second reagent rack 17 and a reader 18. The second reagent rack 17 is located in the reagent storage 15 to hold the second reagent containers 14. The reader 18 is configured to read first reagent information and second reagent information that identify the first reagent and the second reagent, respectively. The first reagent information and the second reagent information are written to the first and second reagent containers 13, 14 held by the first and second reagent racks 16, 17, respectively. The analyzer 10 further includes a plurality of reaction cells 19 which are arranged on the circumference, and a reaction disk 20 for holding the reaction cells 19. Having read the first reagent information and the second reagent information, the reader 18 outputs the pieces of information to the analysis controller 52.

Figure 8:
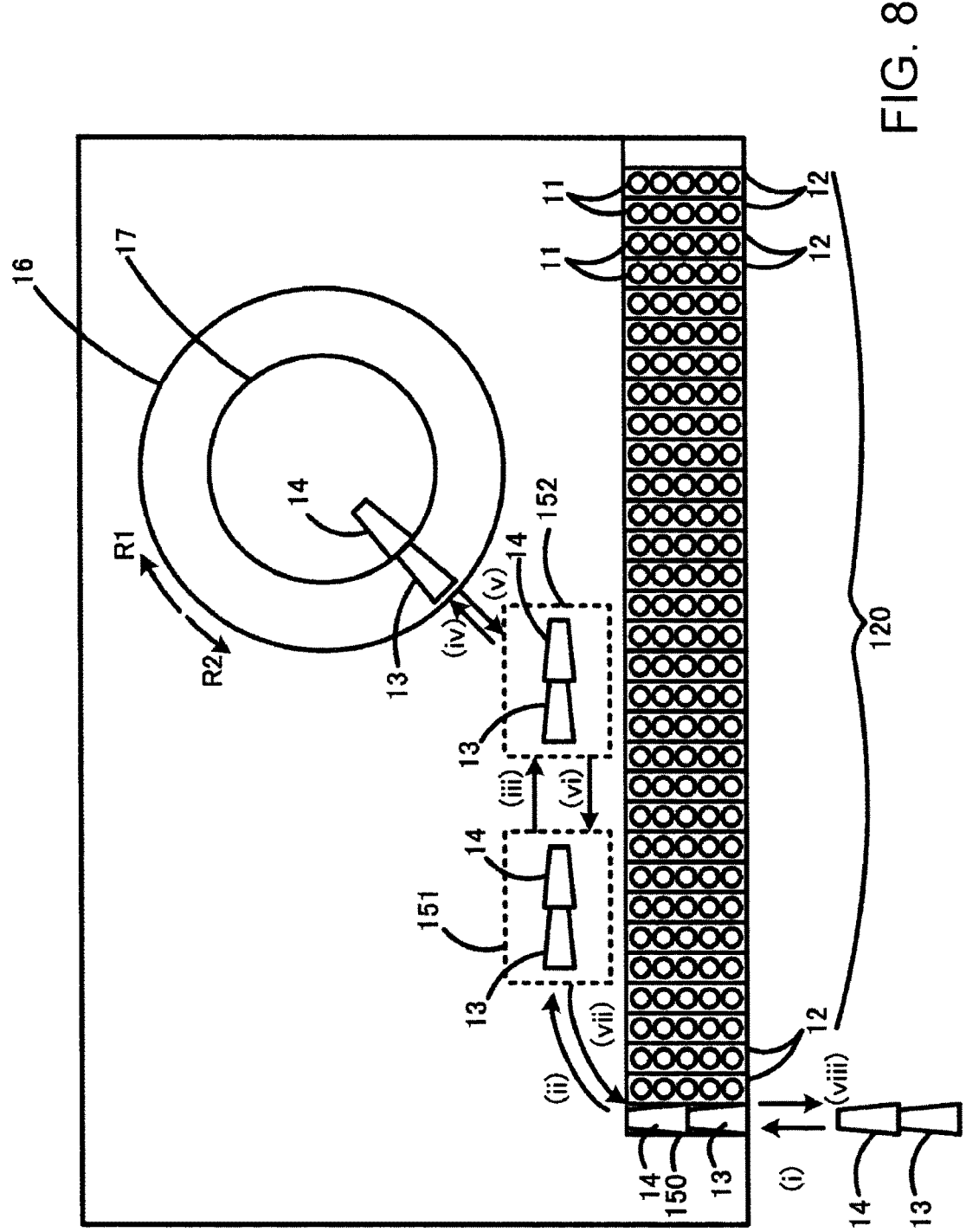
FIG. 8 is a diagram for explaining a configuration for transporting the first and second reagent containers of the embodiment.

On the front of the automated biochemical analyzer 100, a rack sampler 120 is arranged along the front edge (see FIG. 8). The rack sampler 120 is configured to be capable of accommodating the sample racks 12 that are arranged side by side in a row and transporting each of them to a predetermined position. The sample racks 12 each accommodate a plurality of (e.g., five) the sample containers 11. The sample containers 11 retain a sample.

The analyzer 10 further includes a sample dispensing probe 21 and a sample dispensing arm 22 to hold the sample dispensing probe 21. The sample dispensing probe 21 is configured to aspirate a sample in the sample containers 11 held by the sample racks 12 and discharge it into the reaction cell 19 to dispense the sample. The analyzer 10 further includes a first reagent dispensing probe 23 configured to sack the first reagent in the first reagent container 13 marked with the first reagent information read by the reader 18 and discharge it into the reaction cell 19 in which each sample has been discharged to dispense the first reagent.

The analyzer 10 further includes a first reagent dispensing arm 24 that holds the first reagent dispensing probe 23, a first stirrer 25 for mixing a compound liquid of the sample and the first reagent dispensed into the reaction cell 19, a first mixing arm 26 that holds the first stirrer 25, and a second reagent dispensing probe 27. The second reagent dispensing probe 27 is configured to aspirate the second reagent in the second reagent container 14 marked with the second reagent information read by the reader 18 and discharge it into the reaction cell 19 in which each sample and the first reagent have been discharged to dispense the second reagent.

The analyzer 10 further includes a second reagent dispensing arm 28 that holds the second reagent dispensing probe 27, a second stirrer 29 for mixing a compound liquid of the sample, the first reagent and the second reagent in the reaction cell 19, and a second mixing arm 30 that holds the second stirrer 29. The analyzer 10 further includes a measurement unit 31 and a wash nozzle 32. The measurement unit 31 irradiates light to the compound liquid in the reaction cell 19 to optically measure it. The wash nozzle 32 is configured to wash inside the reaction cell 19 after the measurement by the measurement unit 31.

The measurement unit 31 irradiates light to the reaction cell 19. Based on a detection signal for detecting the light having passed through the compound liquid containing the standard sample or the test sample in the reaction cell 19, the measurement unit 31 generates, for example, standard data or test data represented by absorbance and the volume of change in the absorbance. Then, the measurement unit 31 outputs the standard data or the test data to the data processor 60.

The driver 51 illustrated in FIG. 1 has a drive mechanism for driving the sample racks 12 to move the sample containers 11, and a drive mechanism for driving each of the first reagent rack 16 and the second reagent rack 17 independently to move the first and second reagent containers 13, 14, for example, in the horizontal direction. Besides, the driver 51 includes a position detector that detects first and second holding positions where the first and second reagent containers 13, 14 marked with the first and second reagent information read by the reader 18 of the analyzer 10 are held by the first and second reagent racks 16, 17. The driver 51 outputs information on the first and second holding positions thus detected to the analysis controller 52.

The driver 51 also has a drive mechanism for driving the reaction disk 20 to rotationally move the reaction cell 19. Further, the driver 51 has a drive mechanism for driving the sample dispensing arm 22, the first reagent dispensing arm 24, the first mixing arm 26, the second reagent dispensing arm 28, and the second mixing arm 30 to respectively move the sample dispensing probe 21, the first reagent dispensing probe 23, the first stirrer 25, the second reagent dispensing probe 27, and the second stirrer 29. In addition, the driver 51 has a drive mechanism or the like to move the wash nozzle 32 up and down.

The analysis controller 52 includes a storage. Based on the information on the first and second holding positions output from the driver 51 and the first and second reagent information output from the reader 18, the storage stores the information on the first and second holding positions where the first and second reagent containers 13, 14 marked with the first and second reagent information read by the reader 18 are held by the first and second reagent racks 16, 17.

Incidentally, the first and second reagent information and the information on the first and second holding positions where the first and second reagent containers 13, 14 marked with the first and second reagent information are held by the first and second reagent racks 16, 17 may be entered by using the operation unit 80 to store these pieces of information in the storage of the analysis controller 52.

The data processor 60 includes a calculator 61 and a data storage 62. The calculator 61 processes the standard data and the test data generated by the measurement unit 31 of the analyzer 10 to generate calibration data and analysis data of each test assay. The data storage 62 stores the calibration data and the analysis data generated by the calculator 61.

From the standard data generated by the measurement unit 31 and a standard value set in advance for the standard sample of the standard data, the calculator 61 generates the calibration data representing a relationship between the concentration or density and activity of each test assay component and the standard data. The calculator 61 stores the calibration data in the data storage 62 as well as outputting it to the output unit 70.

The calculator 61 also retrieves the calibration data of a test assay corresponding to the test data generated by the measurement unit 31 from the data storage 62. The calculator 61 generates the analysis data represented as the concentration value and the activity value of enzymes from the test data generated by the measurement unit 31 by using the calibration data. The calculator 61 stores the analysis data in the data storage 62 as well as outputting it to the output unit 70.

The data storage 62 includes a memory device such as a hard disk, and stores the calibration data output from the calculator 61 with respect to each test assay. The data storage 62 also stores the analysis data of each test assay output from the calculator 61 with respect to each test sample.

The output unit 70 includes a print unit 71 to print out the calibration data and the analysis data output from the calculator 61 of the data processor 60, and a display 72 to display them. The print unit 71 includes a printer and prints the calibration data and the analysis data output from the calculator 61 on printer paper or the like according to a format set in advance.

The display 72 includes a monitor such as a cathode ray tube (CRT) or a liquid crystal panel, and displays the calibration data and the analysis data output from the calculator 61. The display 72 also displays setting screens including: an analysis parameter setting screen for setting analysis parameters such as sample volume to be dispensed into the reaction cell 19, first reagent volume, and second reagent volume for each test assay; a reagent information setting screen for setting reagent information of the first and second reagents used for the analysis of each test assay; and a test sample information setting screen for selecting and setting subject identification information such as name, ID or the like for identifying each test sample and a test assay for the test sample identified by the identification information with respect to the test sample to be examined.

The operation unit 80 includes an input device such as a keyboard, a mouse, buttons, and a touch key panel. The operation unit 80 is used to enter the analysis parameters of each test assay, the first and second reagent information of reagents used for the analysis of each test assay, and test information such as the subject identification information of a test sample to be examined, test assays, and the like.

The system controller 90 includes a central processing unit (CPU) and a memory circuit. The system controller 90 stores, in the memory circuit, input information provided by operating the operation unit 80, such as a command signal, information on the analysis parameters of each test assay, the first and second reagent information, the subject identification information, and test assay information. Thereby, the system controller 90 performs the overall control of the analysis controller 52, the data processor 60, and the output unit 70 based on the input information to control the entire system.

Figure 9:
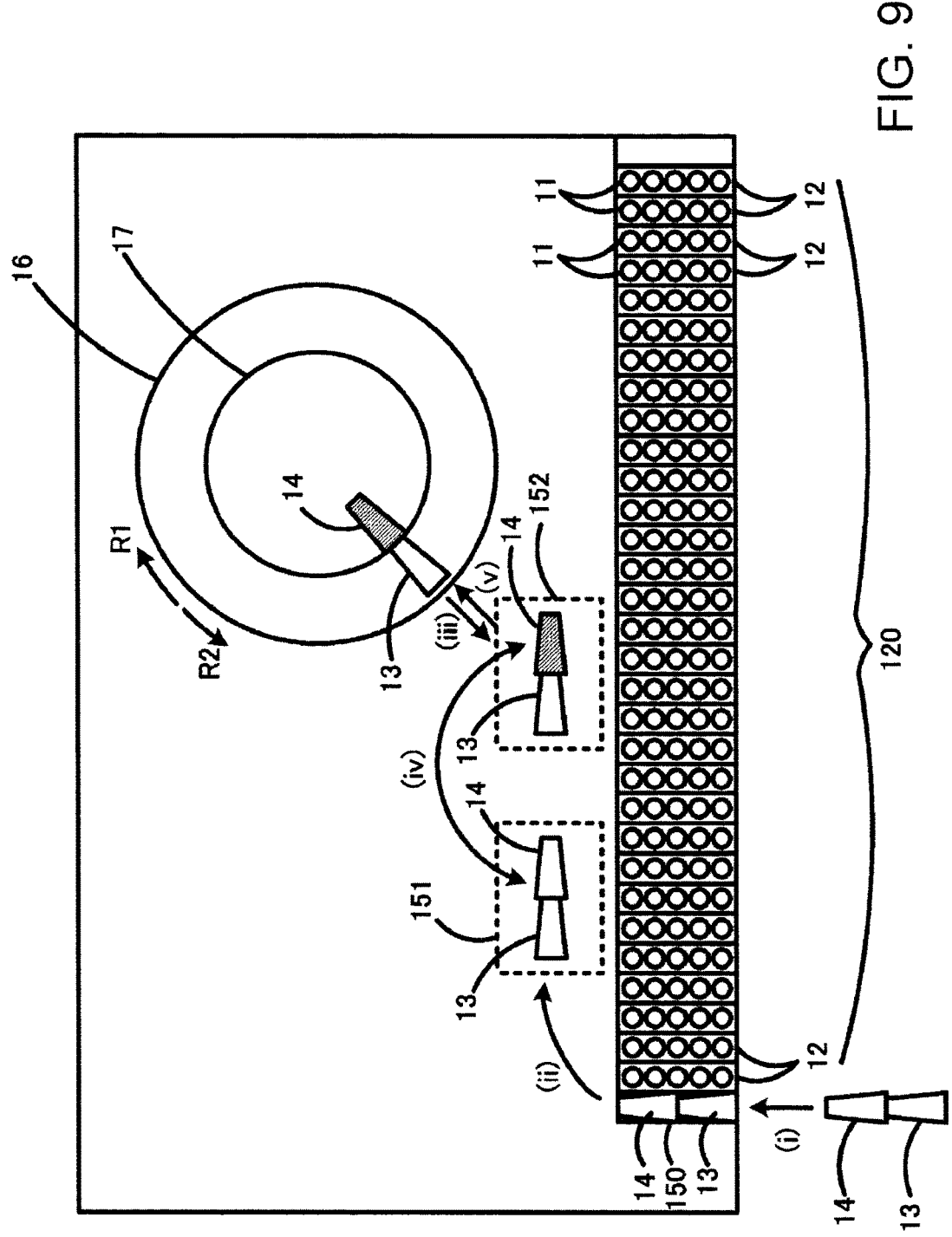
FIG. 9 is a diagram for explaining a configuration for replacing the first or second reagent container of the embodiment.

Next, with reference to FIGS. 8 and 9, a description is given of a mechanism for transporting/replacing the first reagent containers 13 and/or the second reagent containers 14. FIG. 8 is an explanatory diagram of a configuration for transporting the first reagent containers 13 and the second reagent containers 14 of the embodiment.

As illustrated in FIG. 8, a transport rack 150 is arranged in the end position of the rack sampler 120. The first reagent container 13 and the second reagent container 14 are coupled together by a connection between a first support 131 and a second support 141, and transported to/from the transport rack 150 manually or by a robotic arm (not illustrated) (see (i), (viii) in FIG. 8). The robotic arm may sometimes be simply referred to as "arm". The first support 131 and the second support 141 correspond to an example of "support". The first support 131 and the second support 141 are configured to be connectable to and disconnectable from each other. This connectable/disconnectable structure of the first support 131 and the second support 141 is described later.

As illustrated in FIG. 8, in the automated biochemical analyzer 100, a first stage 151 and a second stage 152 are arranged in a space between the transport rack 150 and the first reagent rack 16/the second reagent rack 17. The first stage 151 and the second stage 152 are configured such that the first reagent container 13 and the second reagent container 14, in which the first support 131 and the second support 141 are connected to each other, can be temporarily placed thereon.

A transporter (not illustrated) is provided to transport the first reagent container 13 and the second reagent container 14 from the transport rack 150 to the first stage 151 and vice versa (see (ii), (vii) in FIG. 8). Further, a transporter (not illustrated) is provided to transport the first reagent container 13 and the second reagent container 14 from the first stage 151 to the second stage 152 and vice versa (see (iii), (vi) in FIG. 8). Still further, a transporter (not illustrated) is provided to transport the first reagent container 13 and the second reagent container 14 from the second stage 152 to the first reagent rack 16/the second reagent rack 17 and vice versa (see (iv), (v) in FIG. 8). For example, these transporters may be formed of one robotic arm or a plurality of robotic arms.

The transporter (e.g., the arm) enables the transport of the first reagent container 13 and the second reagent container 14 from the transport rack 150 through the first stage 151 and the second stage 152 to the first reagent rack 16/the second reagent rack 17. The transporter (arm) also enables the transport of the first reagent container 13 and the second reagent container 14 from the first reagent rack 16/the second reagent rack 17 through the second stage 152 and the first stage 151 to the transport rack 150. When the first reagent container 13 and the second reagent container 14 are transported from the first reagent rack 16/the second reagent rack 17 to the second stage 152, the driver 51 moves, in advance, the first reagent container 13 and the second reagent container 14 to extraction positions C1 and C2, respectively, and the first support 131 and the second support 141 are engaged together (i.e., the supports are connected to each other upon extraction of the containers). This is described later.

FIG. 9 is an explanatory diagram of a configuration for replacing the first reagent container 13 or the second reagent container 14 of the embodiment. The transporter (arm) enables the replacement of the first reagent container 13 on the first stage 151 and the first reagent container 13 on the second stage 152 as well as the replacement of the second reagent container 14 on the first stage 151 and the second reagent container 14 on the second stage 152 (see (iv) in FIG. 9). At this time, in the first stage 151, the first support 131 and the second support 141 are disengaged, and thereafter, engaged again (i.e., the supports are disengaged, and after that reconnected). Similarly, in the second stage 152, the first support 131 and the second support 141 are disengaged, and thereafter, engaged again (i.e., the supports are disengaged, and after that reconnected).

In the replacement of the first reagent container 13 or the second reagent container 14, the containers move relative to each other regardless of which of them is to be replaced. Therefore, assuming that the second reagent container 14 on the second reagent rack 17 is to be replaced, an example is described of the replacement of the second reagent container 14 (replaced) with another second reagent container 14 (replacing) in reference to FIG. 9. In FIG. 9, the second reagent container 14 to be replaced is indicated by hatching. Incidentally, it is assumed that the driver 51 moves, in advance, the first reagent container 13 on the first reagent rack 16 and the second reagent container 14 (replaced) to the extraction positions C1 and C2, respectively, and the first support 131 and the second support 141 are engaged together (i.e., the supports are connected to each other).

First, the first reagent container 13 and the second reagent container 14 (replacing) are transported by the transporter (arm) or manually to the transport rack 150 (see (i) in FIG. 9). Next, the first reagent container 13 and the second reagent container 14 (replacing) are transported by the transporter (arm) from the transport rack 150 to the first stage 151 (see (ii) in FIG. 9).

Then, the first reagent container 13 and the second reagent container 14 (replaced) are transported by the transporter (arm) from the first reagent rack 16/the second reagent rack 17 to the second stage 152 (see (iii) in FIG. 9). Since the first support 131 of the first reagent container 13 and the second support 141 of the second reagent container 14 (replaced) are engaged with each other in advance (i.e., the supports have been connected to each other for extraction), the first reagent container 13 and the second reagent container 14 (replaced) can be simultaneously extracted from the reagent storage 15. In FIG. 9, the second reagent container 14 (replaced) on the second stage 152 is indicated by hatching.

After that, by using the transporter (arm), the second reagent container 14 (replaced) on the second stage 152 is replaced with the second reagent container 14 (replacing) on the first stage 151 (see (iv) in FIG. 9). Thereby, in the first stage 151, the second support 141 of the second reagent container 14 (replaced) and the first support 131 of the first reagent container 13 are engaged together (i.e., the supports are connected to each other). Further, in the second stage 152, the second support 141 of the second reagent container 14 (replacing) and the first support 131 of the first reagent container 13 are engaged together (i.e., the supports are connected to each other).

Then, the first reagent container 13 and the second reagent container 14 (replacing) are transported by the transporter (arm) from the second stage 152 to the first reagent rack 16/the second reagent rack 17 (see (v) in FIG. 9). Thus, one reagent container (14) can be replaced with another reagent container (14).

In the following, a description is given of a configuration of the first and second reagent racks 16, 17 and the first and second reagent containers 13, 14 of the analyzer 10 and the operation of the automated biochemical analyzer 100.

Described first below are the configuration and operation of the first and second reagent racks 16, 17 that hold the first and second reagent containers 13, 14.

FIG. 3 is a plan view illustrating a configuration of the first and second reagent racks 16, 17 that hold the first and second reagent containers 13, 14. The first reagent rack 16 is in a disk shape having a circular opening in the center. The first reagent rack 16 includes a plurality of partition plates arranged radially on the upper surface to be capable of holding the first reagent containers 13 in a loose fit without a displacement. Thus, the first reagent rack 16 holds an array of the first reagent containers 13, each arranged between an adjacent pair of the partition plates, along the circumference of the outer circle of the concentric circles.

The second reagent rack 17 is arranged on the inner circumference side in proximity to the first reagent rack 16. The second reagent rack 17 includes a plurality of partition plates arranged radially on the upper surface to be capable of holding the second reagent containers 14 in a loose fit without a displacement. Thus, the second reagent rack 17 holds an array of the second reagent containers 14, each arranged between an adjacent pair of the partition plates, along the circumference of the inner circle of the concentric circles.

The driver 51 drives the first and second reagent racks 16, 17 independently. Accordingly, the first and second reagent containers 13, 14 move independently of each other in directions R1 and R2 that correspond to the arrangement direction of them. Either one of the first reagent container 13 held by the first reagent rack 16 and the second reagent container 14 held by the second reagent rack 17 is moved in proximity to the other reagent containers.

The reader 18 reads the first and second reagent information written to the first and second reagent containers 13, 14 held by the first and second reagent racks 16, 17. The driver 51 detects the first and second holding positions where the first and second reagent containers 13, 14 marked with the first and second reagent information read by the reader 18 are held by the first and second reagent racks 16, 17.

The analysis controller 52 controls the driver 51 based on the first and second reagent information read by the reader 18 and the information on the first and second holding positions detected by the driver 51. Thereby, the analysis controller 52 stops the first reagent container 13 held in the first holding position by the first reagent rack 16 at each stop position such as a first suction position T1 where the first reagent dispensing probe 23 can aspirate the reagent, a fourth suction position T4 where the second reagent dispensing probe 27 can aspirate the reagent, and the extraction position C1. Similarly, the analysis controller 52 stops the second reagent container 14 held in the second holding position by the second reagent rack 17 at each stop position such as a second suction position T2 where the second reagent dispensing probe 27 can aspirate the reagent, a third suction position T3 where the first reagent dispensing probe 23 can aspirate the reagent, and the extraction position C2.

By driving the first and second reagent racks 16, 17, independently of each other in this manner, the first reagent container 13 held by the first reagent rack 16 and the second reagent container 14 held by the second reagent rack 17 can be moved to each stop position at the same timing.

Described next are the operation of the automated biochemical analyzer 100 and the configuration of the first and second reagent containers 13, 14.

When there is a shortage of at least either one of the first reagent in the first reagent container 13 held by the first reagent rack 16 and the second reagent, which is paired up with the first reagent, in the second reagent container 14 held by the second reagent rack 17, in response to the input of reagent information such as test assay name or the like for identifying the reagent in short supply provided through the operation unit 80, the analysis controller 52 controls the driver 51 based on the input information.

The analysis controller 52 controls the driver 51 to drive the first and second reagent racks 16, 17 based on the first and second reagent information from the reader 18 and the information on the first and second holding positions from the driver 51 such that the first and second reagent containers 13, 14, which are respectively marked with the first and second reagent information related to the input reagent information, stop at the extraction positions C1, C2 where they come in proximity to each other.

By driving the first and second reagent racks 16, 17, independently of each other in this manner, it is possible to stop a pair of the first and second reagent containers 13, 14, in which at least one of the first reagent and the second reagent that is paired up with the first reagent is insufficient, at the extraction positions C1, C2.

Figure 4A:
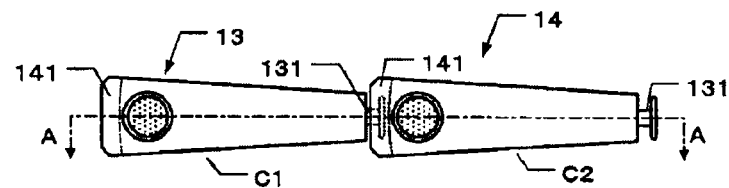
FIGS. 4A and 4B are diagrams of the first and second reagent containers held by the first and second reagent racks that stop at a position in the embodiment.
Figure 4B:
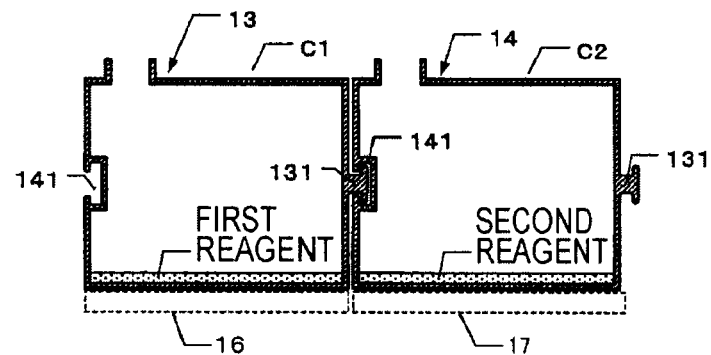

FIGS. 4A and 4B illustrate the first and second reagent containers 13, 14 held by the first and second reagent racks 16, 17 stopped at the extraction positions C1, C2. FIG. 4A is a plan view of the first and second reagent containers 13, 14 at the extraction positions C1, C2. FIG. 4B is a cross-sectional view taken along line A-A in FIG. 4A.

The first reagent container 13 has an opening on the top to allow the first reagent dispensing probe 23 to enter the opening to aspirate the first reagent. A label describing the first reagent information is attached to the first reagent container 13. The label is attached in a predetermined position on the outer surface where the reader 18 can read the first reagent information from the first reagent container 13 held by the first reagent rack 16. The first reagent information may be, for example, a bar code for identifying the first reagent. Similarly, the second reagent container 14 has an opening on the top to allow the second reagent dispensing probe 27 to enter the opening to aspirate the second reagent. A label describing the second reagent information for identifying the second reagent is attached to the second reagent container 14. The label is attached in a predetermined position on the outer surface where the reader 18 can read the second reagent information from the second reagent container 14 held by the second reagent rack 17.

The first reagent container 13 is provided with the first support 131 having, for example, a convex shape on one outer side surface on the inner circumference side, which comes in proximity to the second reagent container 14 in the extraction position C2 when the container 13 is located in the extraction position C1. On the other hand, the second reagent container 14 is provided with the second support 141 having a concave shape on one outer side surface on the outer circumference side, which comes in proximity to the first reagent container 13 in the extraction position C1 when the container 14 is located in the extraction position C2. The second support 141 is configured to engage the first support 131 of the first reagent container 13. The first support 131 in a convex shape and the second support 141 in a concave shape engage each other in the extraction positions C1, C2, and thereby they are connected to each other. When any one of the first support 131 in a convex shape and the second support 141 in a concave shape is moved from the extraction position C1 or C2 to direction R1 or R2 (see FIG. 3), the supports are disengaged. Incidentally, the second support 141 may be arranged on one outer side surface of the first reagent container 13, and the first support 131 may be arranged on one outer side surface of the second reagent container 14.

Figure 5:
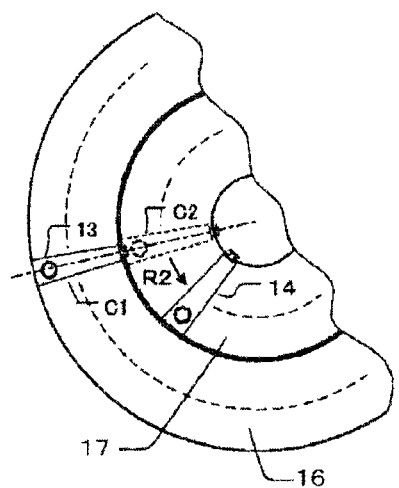
FIG. 5 is a diagram of the second reagent container moved from the position in the embodiment.

In the first and second reagent containers 13, 14 at the extraction positions C1, C2, the one outer side surface on the inner circumference side and the first support 131 and the one outer side surface on the outer circumference side and the second support 141 are located in close proximity to each other but slightly apart. Therefore, as illustrated in FIG. 5, the driver 51 may drive the second reagent rack 17 to move the second reagent container 14 from the extraction position C2, for example, in the direction R2 in close proximity to the first reagent container held by the first reagent rack 16. By moving the second reagent container 14 from the extraction position C2 in the direction R2, the reagent racks (the first reagent rack 16, the second reagent rack 17) allow disengagement between the supports (here, the first support 131 in a convex shape, the second support 141 in a concave shape) to provide the second reagent container 14 for analysis.

Similarly, as illustrated in FIG. 5, the driver may drive the first reagent rack 16 to move the first reagent container 13 from the extraction position C1, for example, in the direction R1 (see FIG. 3) in close proximity to the second reagent container 14 held by the second reagent rack 17. By moving the first reagent container 13 from the extraction position C1 in the direction R1 (see FIG. 3), the reagent racks (the first reagent rack 16, the second reagent rack 17) allow disengagement between the supports (here, the first support 131 in a convex shape, the second support 141 in a concave shape) to provide the first reagent container 13 for analysis.

The first reagent container 13 and the second reagent container 14 have the same shape and size. One of the first reagent container 13 and the second reagent container 14 is provided with one of the first support 131 and the second support 141 on one outer side surface and the other of the supports on the other outer side surface. The other reagent container is provided with the other support on one outer side surface and the one of the supports on the other outer side surface.

That is, the first reagent container 13 is provided with the second support 141 on the other outer side surface on the outer circumference side which, when the container 13 is stopped at the extraction position C2 as being held by the second reagent rack 17, comes in proximity to the second reagent container 14 stopped at the extraction position C1 as being held by the first reagent rack 16. On the other hand, the second reagent container is provided with the first support 131 on the other outer side surface on the inner circumference side which, when the container 14 is stopped at the extraction position C1 as being held by the first reagent rack 16, comes in proximity to the first reagent container 13 stopped at the extraction position C2 as being held by the second reagent rack 17.

Incidentally, the first reagent container 13 may be held by the second reagent rack 17, and the second reagent container 14 may be held by the first reagent rack 16. In this case, the first reagent container 13 held by the second reagent rack 17 is stopped at the third suction position T3 so that the first reagent dispensing probe 23 can aspirate the first reagent. The second reagent container 14 held by the first reagent rack 16 is stopped at the fourth suction position T4 so that the second reagent dispensing probe 27 can aspirate the second reagent.

As described above, the first reagent container is provided with the first and second supports 131, 141, and the second reagent container 14 is also provided with the first and second supports 131, 141 and has the same shape and size as the first reagent container 13. Thereby, the containers can be used for both the first reagent and the second reagent. Besides, when one of the first and second reagent containers 13, 14 is held by one of the first and second reagent racks 16, 17, the other of them can be held by the other rack, and thus the first and second reagents can be aspirated by the first and second reagent dispensing probes 23, 27.

The operator of the automated biochemical analyzer 100 may pick the first reagent container 13 stopped at the extraction position C1 or the second reagent container 14 stopped at the extraction position C2 and move it upward in a direction other than the directions R1 and R2 in which the container is driven to move by the driver 51. With this, the support provided to one of the reagent containers supports the one provided to the other of the reagent containers in proximity to the support to move the other reagent container upward.

Incidentally, there may be provided a transporter including a grasper and an arm. The grasper is capable of grasping one of the reagent containers at the extraction position C1 or C2. The arm is capable of moving the grasper upward to the height where the one of the reagent containers grasped by the grasper and the other reagent container supported by it are located above the first and second reagent racks 16, 17 and the reagent storage 15. The transporter may move the first and second reagent containers 13, 14 stopped at the extraction positions C1, C2 out of the first and second reagent racks 16, 17 and the reagent storage as well as transporting the first and second reagent containers 13, 14 containing a sufficient volume of the first and second reagents to the extraction positions C1, C2.

As described above, the first and second reagent containers 13, 14 each having the first and second supports 131, 141 are paired and stopped at the extraction positions C1, C2. One of the reagent containers at the extraction position C1 or C2 is moved upward in a direction other than the directions in which the container is driven to move by the driver 51. In this manner, the other reagent container can also be moved in the same direction simultaneously with the reagent container.

This enables a pair of the first and second reagent containers 13, 14 with a shortage of at least either one of the first and second reagents to be simultaneously extracted from the first and second reagent racks 16, 17 as well as the reagent storage 15. Thus, it is possible to reduce the work of the operator.

Figure 6:
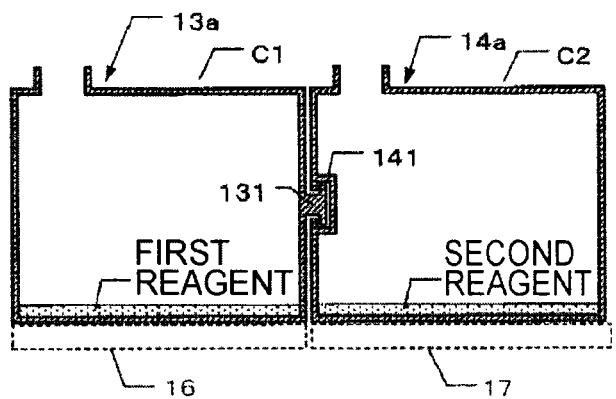
FIG. 6 is a diagram of another example of the first and second reagent containers of the embodiment.

As illustrated in FIG. 6, the first reagent container 13 may be configured without the second support 141. In other words, a first reagent container 13a having the other outer side surface formed of a plane may be used for retaining the first reagent and held by the first reagent rack 16. Similarly, the second reagent container 14 may be configured without the first support 131. Specifically, a second reagent container 14a having the other outer side surface formed of a plane may be used for retaining the second reagent and held by the second reagent rack 17.

In addition, one of the first and second reagent containers 13a, 14a illustrated in FIG. 6 may have a capacity corresponding to one of first and second reagent volumes, the other of which is the volume of the reagent retained in the other reagent container and dispensed into the reaction cell 19.

Figure 7A:
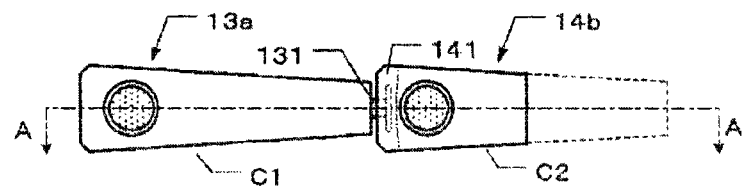
FIGS. 7A and 7B are diagram of an example of the second reagent container having a capacity according to the volume of second reagent with respect to that of first reagent set as an analysis parameter for the first reagent container in the embodiment.
Figure 7B:
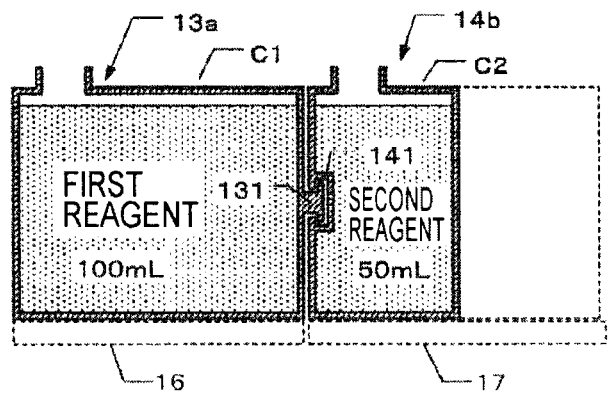

FIGS. 7A and 7B illustrate an example of the second reagent container having a capacity corresponding to the second reagent volume with respect to the first reagent volume that is set as an analysis parameter to the first reagent container 13a. FIG. 7A is a top view of the second reagent container in the extraction position C2. FIG. 7B is a cross-sectional view taken along line A-A in FIG. 7A.

It is assumed that the first reagent volume, i.e., the volume of the first reagent to be dispensed into the reaction cell 19, set as the analysis parameter is 100 μL and the second reagent volume is half of this, and that the first reagent container 13a capable of retaining the first reagent has a capacity of, for example, 100 mL. In this case, a second reagent container 14b has a capacity of 50 mL, which corresponds to the second reagent volume and is half of the capacity of the first reagent container 13a.

The second reagent container 14b is provided with the second support 141 on one outer side surface on the outer circumference side, which comes in proximity to the first reagent container 13a in the extraction position C1 when the container 14b is located in the extraction position C2. The second reagent container 14b is configured such that the other outer side surface formed of a plane on the inner circumference side is closer to the one outer side surface as compared to that of the second reagent container 14a illustrated in FIG. 6.

As described above, the first and second reagent containers 13a, 14b each have a capacity corresponding to the volume of the first or second reagent dispensed into the reaction cell 19. Accordingly, if the first and second reagent containers 13a, 14b retain the first and second reagents in volume as much as their capacities, the first and second reagents run short at approximately the same timing. This reduces the waste of the reagent due to the remainder of the first or second reagent with a smaller value set as the reagent volume.

According to the embodiment described above, the first and second reagent containers 13, 14 provided with the first and second supports 131, 141 are used. One of the first reagent container 13 that retains the first reagent and is held by the first reagent rack 16 and the second reagent container 14 that retains the second reagent, which is paired up with the first reagent, and is held by the second reagent rack 17 can be moved in close proximity to the other of them.

The first and second reagent containers 13, 14 in a pair are controlled to be stopped at the extraction positions C1, C2 where they come in proximity to each other. One of the reagent containers at the extraction position C1 or C2 is moved upward in a direction other than the directions in which the container is driven to move by the driver 51. Thus, the other reagent container can also be moved in the same direction simultaneously with the one of the reagent containers.

This enables a pair of the first and second reagent containers 13, 14 with a shortage of at least either one of the first and second reagents to be simultaneously extracted from the first and second reagent racks 16, 17 as well as the reagent storage 15. Thus, it is possible to reduce the reagent replacement work.

In the above embodiment, an example is described in which the first reagent container 13 and the second reagent container 14 are simultaneously extracted from the reagent storage 15 formed of double racks of the first reagent rack 16 and the second reagent rack 17. However, this is not so limited. Three or more reagent containers may be simultaneously extracted from the reagent storage 15 formed of triple or more reagent racks.

For example, a third reagent rack that can be driven in the same direction as the first reagent rack 16 is provided independently on the outer circumference of the first reagent rack 16. The first and second reagent racks 16, 17 hold the first and second reagent containers 13, 14 that retain the first and second reagents of three-reagent system. The third reagent rack holds a third reagent container that retains a third reagent and has the same shape and size as the first and second reagent containers 13, 14. The first and second reagent containers 13, 14 that retain the first and second reagents of three-reagent system held by the first and second reagent racks 16, 17 are stopped at the extraction positions C1, C2. Along with this, the third reagent container held by the third reagent rack is also stopped at an extraction position in proximity to the first reagent container 13 held by the first reagent rack 16 in the extraction position C1. Then, at least one of the first to third reagent containers stopped at the extraction positions close to one another is moved upward in a direction other than the directions in which the container is driven to move by the driver 51. In this manner, the first to third reagent containers can be extracted simultaneously.

Thus, when at least one of the first to third reagents is insufficient, the first to third reagent containers, which form one set, can be simultaneously extracted from the first to third reagent racks and the reagent storage. As a result, it is possible to reduce the reagent replacement work.

While certain embodiments have been described, these embodiments have been presented by way of example only, and are not intended to limit the scope of the inventions. Indeed, the novel embodiments described herein may be embodied in a variety of other forms; Further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An automated biochemical analyzer configured to dispense a first reagent, a second reagent paired with the first reagent stored inside a reagent storage, and a sample into a reaction cell to measure a compound liquid thereof, the reagent storage comprising:
   a first reagent container configured to retain the first reagent to be dispensed to the reaction cell, and including a first support;
   a second reagent container which is configured to retain the second reagent to be dispensed to the reaction cell, said second reagent container including a second support configured to be connectable to and disconnectable from the first support of the first reagent container that retains the first reagent so that the first reagent container and the second reagent container are connectable to and disconnectable from each other by means of the first and second supports;
   a first reagent rack configured to hold the first reagent container such that the first support can face and engage the second support:
   a second reagent rack configured to hold the second reagent container such that the second support can face and engage the first support, wherein the first and second reagent racks are arranged concentrically: and
   a driver configured to move at least one of the first reagent container and the second reagent container in parallel, and move at least one of the first reagent rack and the second reagent rack in a predetermined direction,
   a controller in communication with the driver, the controller configured to:
   control the driver such that at least one of the first reagent rack and the second reagent rack is driven so that one of the first reagent container and the second reagent container moves independently with respect to the other in a direction in which the first reagent rack or the second reagent rack moves, whereby the movement of the first or second rack disconnects the first support and the second support from each other such that the first reagent container or the second reagent container is able to be used for analysis by the biochemical analyzer; and
   control the driver such that the first reagent rack and the second reagent rack is driven so that one of the first reagent container and the second reagent container moves in parallel with respect to the other container in a direction in which the first reagent rack or the second reagent rack moves so as to connect the first support and second support together for simultaneous extraction of the first and second containers from the reagent storage.

2. The automated biochemical analyzer of claim 1, wherein the first reagent rack and the second reagent rack are driven independently of each other by the driver to move the first reagent container and the second reagent container in parallel.

* * * * *